US011361861B2

(12) United States Patent
Gruemer et al.

(10) Patent No.: US 11,361,861 B2
(45) Date of Patent: Jun. 14, 2022

(54) CONTROLLING CLOUD-BASED IMAGE PROCESSING BY ASSURING DATA CONFIDENTIALITY

(71) Applicant: Siemens Healthcare GmbH, Erlangen (DE)

(72) Inventors: Fabian Gruemer, Nuremberg (DE); Chandrashekara Rangapura Shettappa, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 41 days.

(21) Appl. No.: 16/332,826

(22) PCT Filed: Sep. 16, 2016

(86) PCT No.: PCT/EP2016/072039
§ 371 (c)(1),
(2) Date: Mar. 13, 2019

(87) PCT Pub. No.: WO2018/050247
PCT Pub. Date: Mar. 22, 2018

(65) Prior Publication Data
US 2019/0362836 A1 Nov. 28, 2019

(51) Int. Cl.
*G16H 30/40* (2018.01)
*G06F 3/0488* (2013.01)
(Continued)

(52) U.S. Cl.
CPC ......... *G16H 30/40* (2018.01); *G06F 3/04883* (2013.01); *G06F 21/602* (2013.01); *H04L 67/125* (2013.01)

(58) Field of Classification Search
CPC ........ G16H 10/00; G16H 10/40; G16H 15/00; G16H 20/00; G16H 20/10; G16H 20/13;
(Continued)

(56) References Cited
U.S. PATENT DOCUMENTS 7,421,647 B2    9/2008   Reiner
2011/0087651 A1   4/2011   Westin et al.
(Continued)

FOREIGN PATENT DOCUMENTS

CN         1839618 A    9/2006
CN     102479294 A    5/2012
(Continued)

OTHER PUBLICATIONS

M. Klapperstuck et al., "ContextuWall: Peer Collaboration Using (Large) Displays," 2016 Big Data Visual Analytics (BDVA), Sydney, NSW, 2016, pp. 1-8, doi: 10.1109/BDVA.2016.7787047.*
(Continued)

*Primary Examiner* — Robert W Morgan
*Assistant Examiner* — Charles P Coleman
(74) *Attorney, Agent, or Firm* — Harness, Dickey & Pierce, P.L.C.

(57) ABSTRACT

A method and system are a for gesture support system for controlling a cloud-based image processing application. In an embodiment, the system includes an extended touch screen device; a DICOM Appliance including a receiver and an uploader client, adapted for segregating PHI-data and non-confidential image data, and for encrypting PHI-data and sending a data package, including the encrypted PHI-data and non-confidential image data to a cloud server. The cloud server is adapted for processing the medical image data. It receives the data package form the uploader client and decrypts the received data package. A gesture reception unit receives user-specific gesture signals and a mapping unit maps the received user-specific gesture signals to standard gestures and provides the standard gestures to the cloud server for generating control instructions for the image processing.

30 Claims, 3 Drawing Sheets

(51) Int. Cl.
*G06F 21/60* (2013.01)
*G06F 3/04883* (2022.01)
*H04L 67/125* (2022.01)
*H04L 29/08* (2006.01)

(58) Field of Classification Search
CPC ........ G16H 20/17; G16H 30/00; G16H 40/00;
G16H 50/00; G16H 70/00; G16H 80/00
USPC .................................................. 705/3, 2, 20
See application file for complete search history.

(56) References Cited

U.S. PATENT DOCUMENTS

| | | | |
|---|---|---|---|
| 2011/0093820 A1* | 4/2011 | Zhang | A63F 13/77 715/863 |
| 2011/0169726 A1* | 7/2011 | Holmdahl | G06K 9/00342 345/156 |
| 2012/0134554 A1 | 5/2012 | Dirckx | |
| 2012/0229383 A1 | 9/2012 | Hamilton et al. | |
| 2013/0106686 A1* | 5/2013 | Bennett | G06F 3/017 345/156 |
| 2013/0132856 A1* | 5/2013 | Binyamin | G06F 3/017 715/740 |
| 2013/0159939 A1* | 6/2013 | Krishnamurthi | G06F 3/011 715/863 |
| 2015/0186004 A1* | 7/2015 | Gordon | G01C 21/367 345/173 |
| 2015/0212676 A1 | 7/2015 | Khare | |
| 2016/0154977 A1* | 6/2016 | Jagadish | G06F 21/6254 726/26 |
| 2017/0123487 A1* | 5/2017 | Hazra | G06F 1/163 |
| 2017/0255272 A1* | 9/2017 | Flagg | G06F 3/04883 |
| 2018/0064505 A1* | 3/2018 | Zhao | A61B 6/00 |
| 2018/0164988 A1* | 6/2018 | Sinn | G06F 3/04845 |
| 2019/0075130 A1* | 3/2019 | Petry | H04L 63/1483 |
| 2019/0262094 A1* | 8/2019 | Zhao | G16H 20/40 |

FOREIGN PATENT DOCUMENTS

| | | |
|---|---|---|
| CN | 102713913 A | 10/2012 |
| CN | 103530524 A | 1/2014 |
| WO | WO-2004/102949 A1 | 11/2004 |
| WO | WO 2011085813 A1 | 7/2011 |

OTHER PUBLICATIONS

Xiang Meng, Chung-Ming Cheung, Ka-Lok Ho, King-Shan Lui, E. Y. Lam and V. Tam, "Building smart cameras on mobile tablets for hand gesture recognition," 2012 Sixth International Conference on Distributed Smart Cameras (ICDSC), Hong Kong, 2012, pp. 1-5.*
Soutschek et al., "3-D gesture-based scene navigation in medical imaging applications using Time-of-Flight cameras," 2008 IEEE Computer Society Conference on Computer Vision and Pattern Recognition Workshops, 2008, pp. 1-6, doi: 10.1109/CVPRW.2008.4563162.*
Madhavanath, Sriganesh et al., "GeCCo: Finger gesture-based command and control for touch interfaces," 2012 4th International Conference on Intelligent Human Computer Interactions (HCI), 2012.*
Lamberti, Fabrizio et al., "Adding pluggable and personalized natural control capabilities to existing applications." Sensors (Basel, Switzerland) vol. 15,2 2832-59. Jan. 28, 2015, doi:10.3390/s150202832.*
International Search Report PCT/ISA/210 for International Application No. PCT/EP2016/072039 dated Jun. 22, 2017.
Written Opinion of the International Searching Authority PCT/ISA/237 for International Application No. PCT/EP2016/072039 dated Jun. 22, 2017.
Chinese Office Action dated Aug. 23, 2021 issued in Chinese Patent Application No. 201680089190.6.
European Office Action dated Jan. 27, 2021, for counterpart European Patent Application No. 16 770 473.3.

* cited by examiner

CONTROLLING CLOUD-BASED IMAGE PROCESSING BY ASSURING DATA CONFIDENTIALITY

PRIORITY STATEMENT

This application is the national phase under 35 U.S.C. § 371 of PCT International Application No. PCT/EP2016/072039 which has an International filing date of Sep. 16, 2016, which designated the United States of America, the entire contents of which are hereby incorporated herein by reference.

FIELD

Embodiments of the present invention generally relate to a method and system for controlling cloud-based image processing by assuring data confidentiality, in particular for PHI data (protected health information), comprising data identifying the patient, like name, address, place etc.

BACKGROUND

Advanced image processing was first performed using computer workstations. However, there are several limitations to a workstation-based advanced image processing system. The hardware and software involved with these systems are expensive, and require complicated and time-consuming installations. Because the workstation can only reside in one location, users must physically go to the workstation to use the advanced image processing software and tools. In addition, only one person can use the workstation at a time.

Some have improved on this system by converting the workstation-based advanced image processing system to a network system, a cloud-based system or client-server-based system. These systems offer some improvements over the workstation-based systems in that a user can use the client remotely, meaning the user does not have to be physically located near the server, but can use his/her laptop or computer elsewhere to use the software and tools for advanced image processing. In addition, more than one client can be used with a given server at one time. This means that more than one user can simultaneously and remotely use the software that is installed on one server. The computational power of the software in a client-server-based system is distributed between the server and the client. In a "thin client" system, the majority of the computational capabilities exist at the server. In a "thick client" system, more of the computational capabilities, and possibly data, exist on the client.

As other portable electronic devices (e.g. mobile telephones) have employed touch-sensitive displays (also known as a "touch screens") with a graphical user interface (GUI), one or more processors, memory and one or more modules, programs or sets of instructions stored in the memory for performing multiple functions. In some embodiments, the user interacts with the GUI primarily through finger contacts and gestures on the touch-sensitive display.

Touch-sensitive displays can provide portable electronic devices with the ability to present transparent and intuitive user interfaces for viewing and navigating GUIs and multimedia content. Such interfaces can increase the effectiveness, efficiency and user satisfaction with activities like digital photography on portable electronic devices. In particular, portable electronic devices used for digital photography and digital video may provide the user with the ability to perform various image processing techniques, such as filtering, focusing, exposing, optimizing, or otherwise adjusting captured images—either in real time as the image frames are being captured by the portable electronic device's image sensor or after the image has been stored in the device's memory. Instructions for performing these functions may be included in a computer readable storage medium or other computer program product configured for execution by one or more processors.

Especially, as medical image processing capabilities of portable electronic devices continue to expand and become more complex, software developers of client applications for such portable electronic devices increasingly need to understand how the various inputs and states of the device should be translated into input parameters for the image processing routines.

Medical imaging studies are generated from a variety of sources, including computed tomography, magnetic resonance imaging, ultrasound, and nuclear medicine techniques. Most medical imaging is stored in digital form, using the Digital Imaging and Communications in Medicine (DICOM) storage and transfer protocol to combine originating systems, servers, and networked computers into a Picture Archiving and Communications System (PACS). Since medical DICOM images are different when compared to normal images a different set of medical gestures are used by physicians and radiologists for post processing operations. In addition, these medical DICOM images contain Protected Health information (PHI) data, which may be displayed as annotations on images or which are related to the image data by other ways. When operating these PHI data in a cloud, it is necessary to assure, that the requirements for data confidentiality are met. Operating on these DICOM image needs different set of gestures which the user can configure and use. This raises a need for a system that supports configurable cloud based system to segregate the user specific gestures for handling medical studies to perform medical image viewing, saving and sharing. These user specific gestures can be detected by a gesture detection system and translated into standard gesture input.

Post processing image operations like windowing, applying color LUT, zooming, drawing annotations, drawing region of interest, free drawing, full screen mode viewing, fusion of image etc. require different set of user gestures, which can be configured and mapped to standard gestures. Hospitals have medical products from different vendors, so the gesture support provided by different vendors will be different for the same action like scrolling of images, windowing of images etc. This makes the physicians and radiologists to use different gestures when switching between the devices of different vendors, which in turn is error prone (due to confusions) and takes time. With more complex image processing routines, however, such as graphically intensive image filters, the number and type of inputs, as well as logical considerations regarding the orientation of the device and other factors may become too complex for client software applications to be able to be interpreted and/or processed correctly.

SUMMARY

Accordingly, the inventors have discovered that there is a need for techniques to implement a programmatic interface to map particular user interactions, e.g., gestures, to the standard gestures of medical image processing applications, in a way that provides a seamless, dynamic, and intuitive experience for both the user and the client application software developer, by assuring data confidentiality for PHI information.

According to an embodiment, the present invention is directed to a method for controlling a cloud-based image processing application, comprising:
Providing an extended touch screen device on the client's side for receiving user input configurations for processing the medical image data;
Receiving the medical image data and user-specific gesture signals on the extended touch screen device at a client's side;
Segregating PHI-data and non-confidential data;
Encrypting PHI-data; and
Sending a data package, including encrypted PHI-data and non-confidential data from the client's side to a cloud server; and
Processing the received image data at the cloud server by
Decrypting the received data package
Receiving user-specific gesture signals from the extended touch screen device
Mapping the received user-specific gesture signals to standard gestures and providing the standard gestures to the cloud server for generating control instructions for the image processing application, and
Processing the received image data at the cloud server by applying the control instructions relating to the received user-specific gesture signals.

According to another embodiment of the present invention a method for controlling a cloud-based image processing application is provided, comprising:
providing an extended touch screen device, to receive user input configurations for processing medical image data;
receiving the medical image data and user-specific gesture signals on the extended touch screen device;
segregating PHI-data and non-confidential data of the medical image data;
encrypting the PHI-data;
sending a data package, including encrypted PHI-data and the non-confidential data of the medical image data to a cloud server, the received encrypted PHI-data of the data package being decryptable at the cloud server;
receiving user-specific gesture signals from the extended touch screen device; and
mapping the user-specific gesture signals received to standard gestures and providing the standard gestures to the cloud server for generation of control instructions for the cloud-based image processing application, the image data received at the cloud server being processable by applying the control instructions, relating to the user-specific gesture signals received.

According to another embodiment of the present invention a gesture support system is provided for controlling a cloud-based image processing application, comprising:
An extended touch screen device on the client's side for receiving user input configurations for processing the medical image data;
Access device for accessing a storage with medical image data;
A DICOM Appliance on a client's side with
a receiver, which is adapted for accessing or receiving the medical image data from a storage and
with an uploader client, which is adapted for segregating PHI-data and non-confidential image data and wherein the uploader client is further adapted for encrypting PHI-data and sending a data package, including encrypted PHI-data and non-confidential image data from the uploader client to a cloud server; and
The cloud server which is adapted for processing the medical image data, received from the uploader client, comprising:
an uploader service, which is adapted to receive the data package form the uploader client and to decrypt the received data package
a gesture reception unit which is adapted to receive user-specific gesture signals from the extended touch screen device
a mapping unit which is adapted to map the received user-specific gesture signals to standard gestures and to provide the standard gestures to the cloud server for generating control instructions for the image processing application
A processing unit for processing the received image data by applying the control instructions relating to the received user-specific gesture signals. According to a preferred embodiment of the gesture support system, the extended touch screen device is also adapted to display image data and/or user gestures.

According to another embodiment of the present invention, a gesture support system is provided for controlling a cloud-based image processing application, comprising:
an extended touch screen device to receive user input configurations for processing the medical image data;
at least one processor configured to access a storage storing medical image data;
a DICOM Appliance including a receiver, configured to access or receive the medical image data from the storage, and
an uploader client, configured to segregate PHI-data and non-confidential image data of the medical image data, wherein the uploader client is further configured to encrypt the PHI-data and send a data package, including encrypted PHI-data and the non-confidential image data from the uploader client to a cloud server, the cloud server being configured to process the medical image data, received from the uploader client, and including
an uploader service, configured to receive the data package, including the segregated PHI-data and non-confidential image data of the medical image data, from the uploader client and configured to decrypt the data package received,
a gesture reception unit, configured to receive user-specific gesture signals from the extended touch screen device,
a mapping unit, configured to map the received user-specific gesture signals received to standard gestures and to provide the standard gestures to the cloud server to generate control instructions for the cloud-based image processing application; and
at least one processor to process the received image data by applying the control instructions, relating to the user-specific gesture signals received.

According to another embodiment of the present invention, a gesture support system is provided for controlling a cloud-based image processing application, comprising:
an extended touch screen device to receive user input configurations for processing the medical image data;
at least one processor configured to access a storage storing medical image data;
a DICOM Appliance including a receiver, configured to access or receive the medical image data from the storage, and an uploader client, configured to segregate PHI-data and non-confidential image data of the medical image data, wherein the uploader client is further configured to encrypt the PHI-data and send a data package, including encrypted PHI-data and the non-confidential image data from the uploader client to a cloud server, the cloud server being configured to process the medical image data, received from the uploader client, by receiving the data package, including the segregated PHI-data and non-confidential image data of the medical image data, from the uploader client and decrypting the data package received;

a gesture reception unit, configured to receive user-specific gesture signals from the extended touch screen device;

a mapping unit, configured to map the received user-specific gesture signals received to standard gestures and to provide the standard gestures to the cloud server to generate control instructions for the cloud-based image processing application; and at least one processor to process the received image data by applying the control instructions, relating to the user-specific gesture signals received.

Another embodiment of the invention refers to a computer program being loadable in a memory of a computer, wherein the computer program is adapted to carry out the steps of an embodiment of the method as mentioned above.

Another embodiment to the inventions refers to a non-transitory computer readable medium containing computer-readable instructions stored therein for causing a computer processor to perform the steps of an embodiment of the method, described above.

BRIEF DESCRIPTION OF THE DRAWINGS

The figures illustrate principles of the invention according to specific embodiments. Thus, it is also possible to implement the invention in other embodiments, so that these figures are only to be construed as examples. Moreover, in the figures, like reference numerals designate corresponding modules or items throughout the different drawings.

DETAILED DESCRIPTION OF THE EXAMPLE EMBODIMENTS

Figure 1:
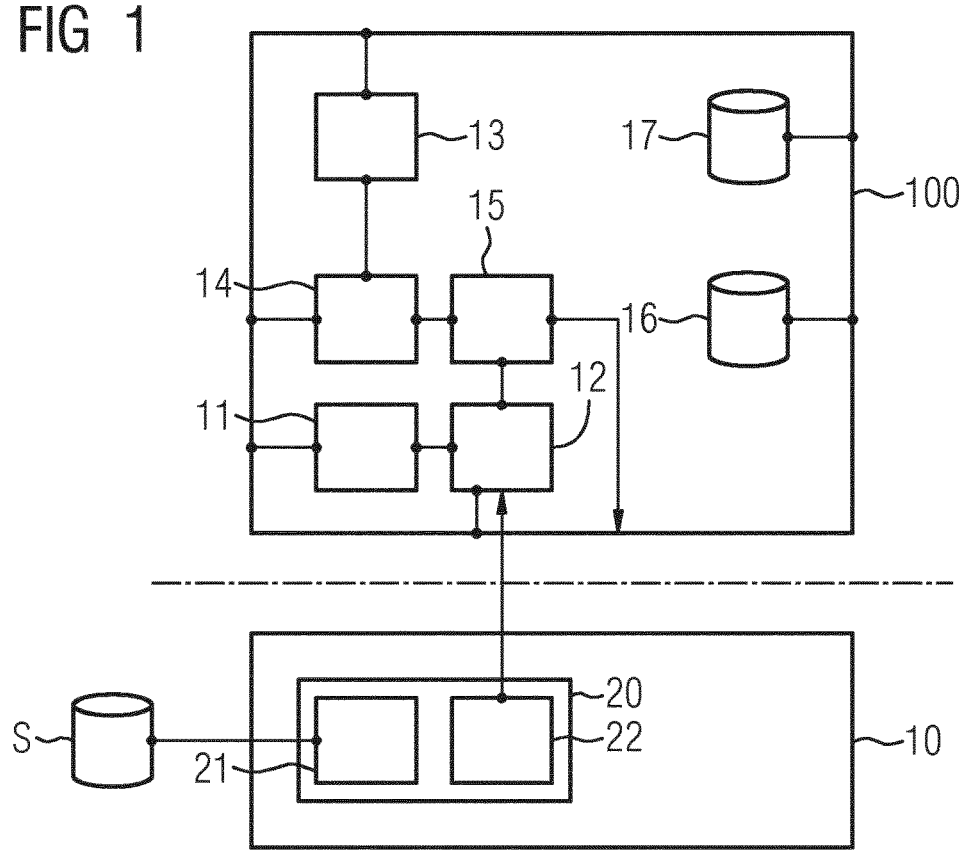
FIG. 1 is a schematic block diagram according to one embodiment of a gesture support system used within a medical environment

According to an embodiment, the present invention is directed to a method for controlling a cloud-based image processing application, comprising:

Providing an extended touch screen device on the client's side for receiving user input configurations for processing the medical image data;

Receiving the medical image data and user-specific gesture signals on the extended touch screen device at a client's side;

Segregating PHI-data and non-confidential data;

Encrypting PHI-data; and

Sending a data package, including of encrypted PHI-data and non-confidential data from the client's side to a cloud server; and Processing the received image data at the cloud server by Decrypting the received data package Receiving user-specific gesture signals from the extended touch screen device Mapping the received user-specific gesture signals to standard gestures and providing the standard gestures to the cloud server for generating control instructions for the image processing application, and Processing the received image data at the cloud server by applying the control instructions relating to the received user-specific gesture signals.

With the proposed solution of an embodiment, the physicians and radiologists can retain their gesture action with new medical systems of different vendors. In addition, physicians and radiologists can keep the same gesture across different vendor medical image processing systems. With the gesture configuration method according to the invention, the mapping of the received user-specific gesture signals to standard gestures may be used to replace existing gestures of the application.

An embodiment of the method comprises processing with an extended touch screen device. The term "extended" is to be construed that a touch screen device is extended with an extension module, so that first gestures may be configured to controlling specific application functions and second the specifically configured user interactions may be receivable and mapped to application control signals.

With other words, the extended touch screen device is used for two different (functional) extensions:

A configuration module is provided for configuring the user input section of the image processing application by receiving user-specific gesture signals for specific instructions and defining the received instructions as input instructions for a specific function—A reception unit is adapted for receiving the configured user-specific gesture signals for application control.

According to another embodiment of the present invention, the processed image is displayed on the client<x>s side and in particular on the extended touch screen device. In this respect, it has to be mentioned that the step of receiving user-specific gesture signals for controlling the cloud-based processing of the application (at least on one server of the cloud) and the step of displaying are functionally interdependent and interrelated.

According to another embodiment of the present invention, the medical image data is provided from a storage, which is provided or hosted at a client's side. The storage may for exam-pie be a local or central PACS System (Picture Archiving and Communication System).

According to another embodiment of the present invention, a configured user input section of the image processing application is transferred from the client's side to the cloud server. This has the technical effect that the user-specific configurations, which he or she has inputted at the local touch screen device are notified to the central cloud server. The user-specific configurations identify those interactions (gestures and gesture patterns) which the user intends to use on her or his local touch screen device for specific functions.

After having configured the user input section, the touch screen device may be used, accordingly, with these configured user-specific gesture signals. According to a preferred embodiment, the user input section may also be reconfigured, in case the user wants to change the gestures or in case he wants to use new gestures as input.

According to another embodiment of the present invention, the received configured user-specific gesture signals are transferred from the client's side to the cloud server for image processing. In this phase, the configured user gestures are used for application control. According to another embodiment of the present invention, the user-specific gesture signals are used as input for at least one of the following functions, selected from the group, consisting of:

Windowing, scrolling, sharing, zooming, inverting, coloring, tapping to select, dragging to select, padding, annotating and/or other image processing input signals.

According to another embodiment of the present invention, the mapping of the received user-specific gesture signals to standard gestures is stored centrally at the cloud server. This aspect is important for providing central access to the mapping of user-specifically configured user input signals and standard user input signals.

According to another embodiment of the present invention, a plurality of distributed computer entities may register to the gesture support system and all or selected registered entities are automatically notified if the cloud server receives new image related data.

Up to now, embodiments of the invention have been described with respect to the method. However, embodiments of the invention also might be implemented in hardware or in hardware modules combined with software modules. The hardware modules are then adapted to perform the functionality of the steps of the method, described above. Accordingly, it is also possible to have a combination of hardware and software modules. The modules are preferably integrated into an existing medical environment, for example into a PACS or RIS (Radiological Information System) or HIS (Hospital Information System) system. Thus, the features claimed or described with respect to the method may also be used within the system and vice versa.

Moreover, those skilled in the art will also appreciate that the functions explained herein may be implemented using individual hardware circuitry, using software functioning in con-junction with a programmed microprocessor or general purpose computer, using an Application Specific Integrated Circuit (ASIC) and/or using one or more Digital Signal Processors (DSP). It will also be appreciated that the present invention may be embodied in a system comprising a computer processor and a memory coupled to the processor, wherein the memory is encoded with one or more programs that may perform the steps disclosed herein.

According to another embodiment of the present invention a gesture support system is provided for controlling a cloud-based image processing application, comprising:

An extended touch screen device on the client's side for receiving user input configurations for processing the medical image data;

Access device for accessing a storage with medical image data;

A DICOM Appliance on a client's side with
  a receiver, which is adapted for accessing or receiving the medical image data from a storage and
  with an uploader client, which is adapted for segregating PHI-data and non-confidential image data and wherein the uploader client is further adapted for encrypting PHI-data and sending a data package, including encrypted PHI-data and non-confidential image data from the uploader client to a cloud server; and The cloud server which is adapted for processing the medical image data, received from the uploader client, comprising:
  an uploader service, which is adapted to receive the data package form the uploader client and to decrypt the received data package
  a gesture reception unit which is adapted to receive user-specific gesture signals from the extended touch screen device
  a mapping unit which is adapted to map the received user-specific gesture signals to standard gestures and to provide the standard gestures to the cloud server for generating control instructions for the image processing application
  A processing unit for processing the received image data by applying the control instructions relating to the received user-specific gesture signals. According to a preferred embodiment of the gesture support system, the extended touch screen device is also adapted to display image data and/or user gestures.

According to a preferred embodiment, the gesture support system comprises access device for accessing storage with medical image data.

According to a preferred embodiment of the gesture support system, the extended touch screen device comprises:
  A configuration extension, which is adapted to configure the user input section of the processing application by receiving user-specific gesture signals for specific instructions and
  A definition extension, which is adapted to define the user interface for the processing application so that it is controlled by the configured user-specific gesture signals.

According to a preferred embodiment the gesture support system further comprises: a storage for storing decrypted image data packages, mappings and/or metadata relating to image processing and/or further comprising a database and/or a service bus.

In a typical clinical scenario medical data is to be protected against unintended access and access from outside the clinical organization or unit. The same holds for employees or personnel working at the institution or working with picture archiving and communication systems ("PACS"), Radiology Information Systems (RIS), Hospital Information Systems (HIS), storage on imaging modalities, workstations, relational databases, fixed content storage systems, and computer files, among other storage systems.

Under certain possible scenarios, the data must be accessible by medical personnel outside of a patient's typical clinic or hospital. It is not uncommon for a hospital to seek outside expert doctors to consult on interpreting lab results and medical images to improve chances of diagnosis. Another scenario requiring image transfer is when a patient is out of his or her normal living area, and another hospital requires use of medical images that are stored at the patient's local hospital. These outside hospitals and doctors require access to the medical information databases inside the doctor's offices and hospitals to make their diagnosis and perform their job. Similarly, a patient may seek an outside doctor's advice himself, either to see a specialist in a field, or to get a second opinion.

These medical studies are viewed my many radiologists, users and physicians. These users use specific gestures for viewing, sharing, saving and post processing of DICOM images. Different users want to use different gestures to perform the same action based on the previously used medical devices, vendor specific gestures, geographical regions, culture and type of user (patient, physician or radiologists).

At least one embodiment of the present invention provides the mechanism to capture user specific gestures and mapping of these user specific gestures to standard gesture actions.

The following graphic shows the mapping file for user specific gesture to standard gesture or to standard user input signals.

These gesture mappings specific to users are stored as xml mapping files in a blob storage in the cloud.

The user can now view, share, save and do post processing on the DICOM studies with his custom gesture and get the same effect as that of standard gesture actions.

In a preferred embodiment, after starting the application it is verified if user specific gestures are to be applied. If not, the standard gestures will be used for application control. Otherwise, the mapping file is read, for mapping user specific gestures to standard user input signals. After receiving a touch gesture it is determined which handle is to be displayed depending on the active application, e.g. tapping to select, dragging to select, tapping/dragging to select. Thereafter, it is determined in which area of the touch display the touch gesture occurred or was received. After this determination the respective handle is determined for display again, as mentioned before and an appropriate manipulation is displayed on the touch screen device. Subsequently, a single touch gesture or multiple of them are received, like dragging, swiping, tapping or other gestures. Finally, the content is manipulated based on the touch gesture and it is determined which action is to be performed depending on the active application, like sharing a study, Color LUT, zooming, inverting or other medical image processing functions.

Embodiments of the invention provide several advantages. A physician may remain those gestures which he is used to know from other applications, he uses and also from applications from different vendors. In addition, he or she may configure his or her own private gestures and use the same within the medical context, which on the long run reduces application processing and service time and is more user friendly. Also gestures may be migrated between different systems, including medical and nonmedical systems.

Gesture mapping techniques in accordance with the various embodiments described herein may be implemented directly by a device's hardware and/or software. The user-specific configured gestures are thus much more intuitive as the original input signals of the application. Further, the user may use those user inputs, which are readily applicable to any number of electronic devices, such as mobile phones, personal data assistants (PDAs), portable electronic devices, monitors, screens, as well as laptops, desktop and tablet computer systems.

Another embodiment of the invention refers to a computer program being loadable in a memory of a computer, wherein the computer program is adapted to carry out the steps of an embodiment of the method as mentioned above.

Another embodiment to the inventions refers to a non-transitory computer readable medium containing computer-readable instructions stored therein for causing a computer processor to perform the steps of an embodiment of the method, described above.

In the following description, there will be described embodiments of a method and system for controlling a cloud-based image processing application. The meaning of specific details should be construed as examples within the embodiments and are not exhaustive or limiting the invention to the precise forms disclosed within the examples. One skilled in the relevant art will recognize that the invention can also be practiced with other modalities or scanners (MR, CT, US AX, PET etc.) and for different post processing applications and without one or more of the specific details or with other methods, implementations, modules, entities, datasets etc. In other instances, well-known structures, computer related functions or operations are not shown or described in detail, as those skilled in the art will understand them.

In the following there is given a short explication and definition of terms, used in this disclosure. The method and system is adapted of an information technological concept in which the processing is executed in the cloud on at least one server or a group of servers and wherein the processing is controlled by user input, which is received on a different device, namely on an extended touch screen device. Therefore, the extended touch screen device and the cloud server (s) need to exchange data with respect to user input and the processed data will be displayed locally on the extended touch screen device as well.

The touch screen device may be integrated into a mobile device like a cellular phone or a touch pad or another mobile device.

Typically medical image data in a DICOM format are to be processed, comprising PHI data and non-PHI data. The first refer to confidential data, which may not leave the borders of a computer system without protection against unintended access and the second refer to non-confidential data. These different forms of data are identified automatically and are processed differently. Therefore, the method and system segregate the PHI data from the rest of the data. This step refers to an automatic separation or isolation of PHI data. The PHI data are encrypted and the non-PHI-data are not encrypted. The latter may be compressed. The encrypted PHI data and the other data are concatenated in order to generate a data pack-age, which is sent to the cloud server. The reception unit at the cloud server, namely the uploader service, is adapted to decrypt the received data package and to extract and unpack the PHI data in order to process the same.

The steps of encrypting and decrypting are related to each other. For this purpose, a symmetric or an asymmetric protocol of a crypto system may be used.

Mapping refers to relating the user-specifically configured gesture signals to other input signals. For example, the function of scrolling or browsing different images may be activated by a user-configured specific gesture, which is defined if the right lower area of the user input is touched. Whereas, usually, the user input for scrolling or browsing is activated by a gesture of a finger movement wiping from the right hand side to the left hand side of the touch screen device. Thus, the latter gesture may be specifically reconfigured with a faster and more effective and precise gesture. This specific gesture is thus stored locally on the touch device as well as centrally on the server in order to control image processing with the new tip gesture.

FIG. 1 shows a schematic block diagram of a gesture support system used within a medical environment.

An extended touch screen device 10 is provided as local client device and comprises a DICOM Appliance 20 and an uploader client 22. The DICOM Appliance 20 comprises a receiver 21, which is adapted for accessing or receiving the medical image data from a storage S. The storage S may be a PACS system, accessible by the extended touch screen device 10. Alternatively, the storage S may be incorporated as local memory within the device.

The uploader client 22 is adapted for segregating PHI-data and non-confidential image data and wherein the uploader client 22 is further adapted for encrypting PHI-data and sending a data package, including encrypted PHI-data and non-confidential image data from the uploader client 22 to a cloud server 100.

The extended touch screen device 10 communicates via a web interface (e.g. SMTP or other protocols, for example proto-cols according to RFC 5321 standard) with at least one cloud server 100. Alternatively, other internet based protocols or web services may be used (e.g. http/https protocols).

The cloud server comprises a gesture reception unit 11, which is adapted to receive user-specific gesture signals from the extended touch screen device 10.

Further, the cloud server 100 comprises an uploader service 12, which is adapted to receive the data package form the uploader client 22 (on the client's side at the extended touch screen device 10) and to decrypt the received data package. Further, the cloud server 100 comprises a mapping unit 14, which is adapted to map the received user-specific gesture signals to standard gestures signals and to provide the standard gestures signals to a processing unit 15 of the cloud server 100 for generating control instructions for the image processing application.

Additionally, the cloud server 100 comprises the processing unit 15 for processing the received image data by applying the control instructions relating to the received user-specific gesture signals.

According to a preferred embodiment, the cloud server 100 may additionally comprise an authorization server 13, which is adapted to verify authorization of entities to execute functions. In particular, the authorization server 13 is adapted to validate the client's device 10 and the processing unit 15 of the cloud server 100 as well as the intended processing functionality.

According to a preferred embodiment, the extended touch screen device 10 is also adapted to display image data and/or user gestures.

According to a preferred embodiment, the extended touch screen device 10 comprises:
  A configuration extension, which is adapted to configure the user input section of the processing application by receiving user-specific gesture signals for specific instructions and
  A definition extension, which is adapted to define the user interface for the processing application so that the processing application is controlled by the configured user-specific gesture signals.

According to a preferred embodiment, the cloud server 100 may additionally comprise a storage 16 for storing decrypted image data packages, mappings and/or metadata relating to image processing.

According to another preferred embodiment the cloud server 100 may additionally comprise a database 17 for storing gesture related data.

According to another preferred embodiment the cloud server 100 may additionally comprise a service bus.

According to another preferred embodiment, the cloud server 100 may additionally comprise an authorization server 13, which is adapted to verify authorization of entities to execute functions.

Figure 2:
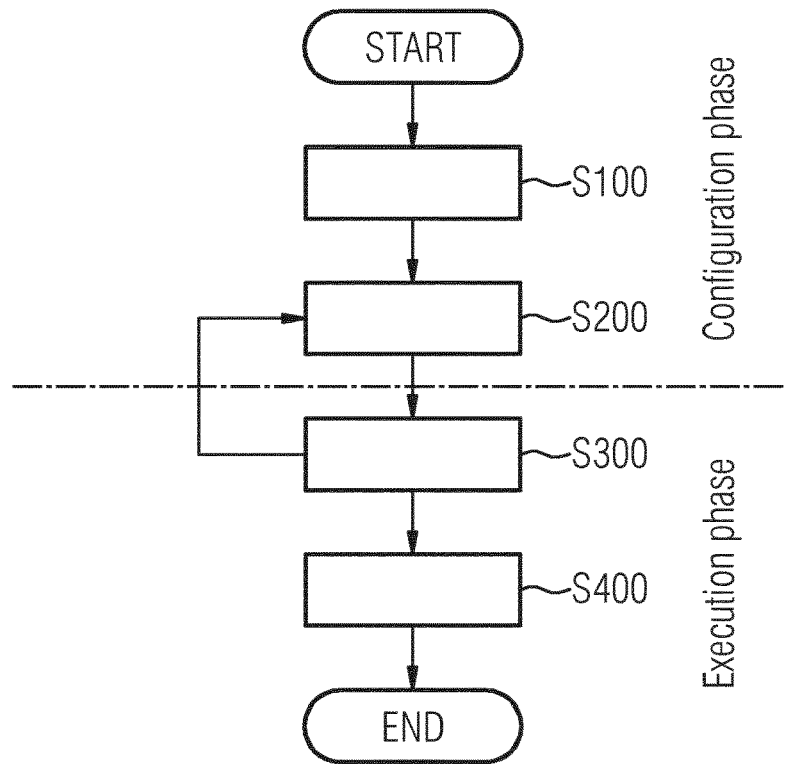
FIG. 2 is a flowchart diagram according to one embodiment of a gesture support method

FIG. 2 shows the general phases of the method according to an embodiment of the invention.

In step S100 the extended touch screen device 10 is provided, which means a touch screen device with extended functionality for gesture configuration. The extended touch screen device 10 is provided at the client' side for:
  Receiving user input configurations (in a configuration phase)
  For receiving user input gestures according to the user input configurations (in an execution phase) and
  For displaying cloud-processed image data.

In step S200 the user input configurations are received on the extended touch screen device 10. This step refers to user-specific configuration of gestures (e.g. finger tipping for scrolling instead of finger wiping).

In step S300 the configurations, which have been defined before in step S200 are applied for control of the cloud based image-processing application. In step S300 the image processing application is controlled and activated by the specifically configured user gestures.

In step S400, the configurations are registered and stored on a cloud storage 16 or in a database 17.

The steps S300 and S200 may be executed in sequence in order to re-configure the gestures again. Then, the new gestures are stored in the cloud (S400).

Figure 3:
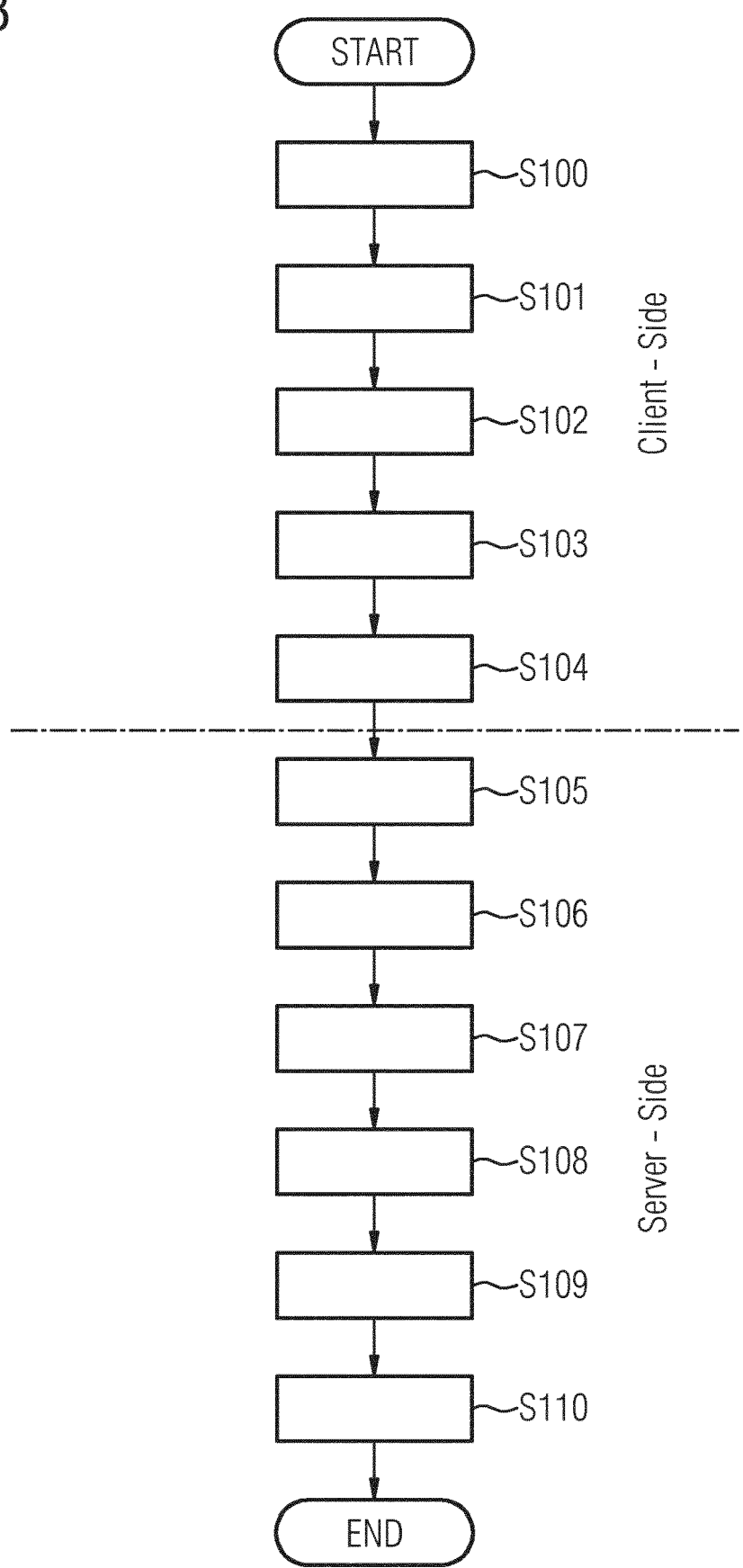
FIG. 3 shows a flowchart for automatically mapping user-configured gestures to gestures signals for cloud-based medical image processing

FIG. 3 shows a flow chart according to an embodiment of the gesture control method of present invention.

In step S100, the extended touch screen device 10 is provided.

In step S101, the medical image data and the user configurations, in particular, the user-specific gesture signals are received at the extended touch screen device 10.

In step S102, the PHI-data and non-confidential data are segregated.

In step S103, the PHI-data are encrypted. In step S104 a data package is generated and sent from the client's side (the uploader client 22) to the cloud server 100 (in particular the uploader service 12), including encrypted PHI-data and non-confidential data.

Steps S100 until S104 are executed locally on the client's side, on the side of the extended touch screen device 10. The following steps S105 until S110 are executed at the cloud server 100.

In step S105, the received data package is decrypted.

In step S106 user-specific gesture, signals are received from the extended touch screen device 10. In this respect, it has to be mentioned, that the time for receiving the user-specific gesture signals on the extended touch screen device 10 may be different from the time for receiving the same at the gesture reception unit 11 in the cloud 100.

In step S107, the received user-specific gesture signals are mapped to standard gestures or standard input signals. The standard input signals are provided to the processing unit 15 of the cloud server 100 for generating control instructions in step S108 for the image processing application.

In step S109, the received image data are processed at the cloud serer 100 by applying the control instructions relating to the received user-specific gesture signals.

In step S110, the processed image is displayed at the client's side the extended touch screen device 10.

Figure 4:
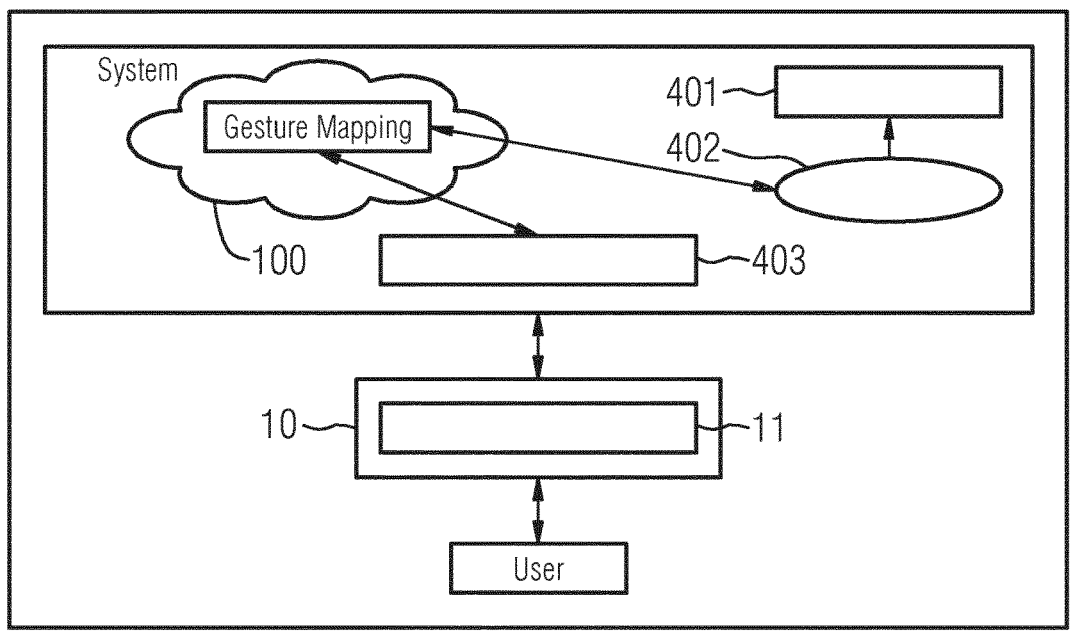
FIG. 4 shows a components diagram of a gesture support system and FIG. 5 is an example of a window for mapping user-configured and standard gestures on the device.

FIG. 4 shows a components diagram with gesture receiver or gesture reception unit 11, incorporated into the extended touch screen device 10, which is applicable by a user. On the cloud-side there is provided the gesture mapping and manipulation component within the cloud server 100, which interacts with a user interface component 403. The cloud server 100 additionally interacts with a content manipulation component 401 and with an interaction type 402.

The interaction type 402 may be provided in the cloud in a centralized manner and can be accessed from all systems. The interaction type 402 is adapted in order to specify details with respect to the kind of interaction for the gesture (e.g. single touch, double touch, drag left to right or right to left, draw a pattern gesture, pinch gesture or user input for controlling the application or user input for receiving data or input within a specific protocol, e.g. a challenge response protocol). The manipulation component is adapted for manipulating the dis-play on the extended touch screen device 10 in response to the received user gesture as input data. It thus refers to modifying content that should be shown after the interaction has been performed. For example, if the user has input a user configured scroll gesture, the display will change correspondingly, so that the next images will be displayed, which has been specified with the scroll instruction. The user interface component receives all different user gestures sent by touch gesture receiver on the extended touch screen device 10.

Figure 5:
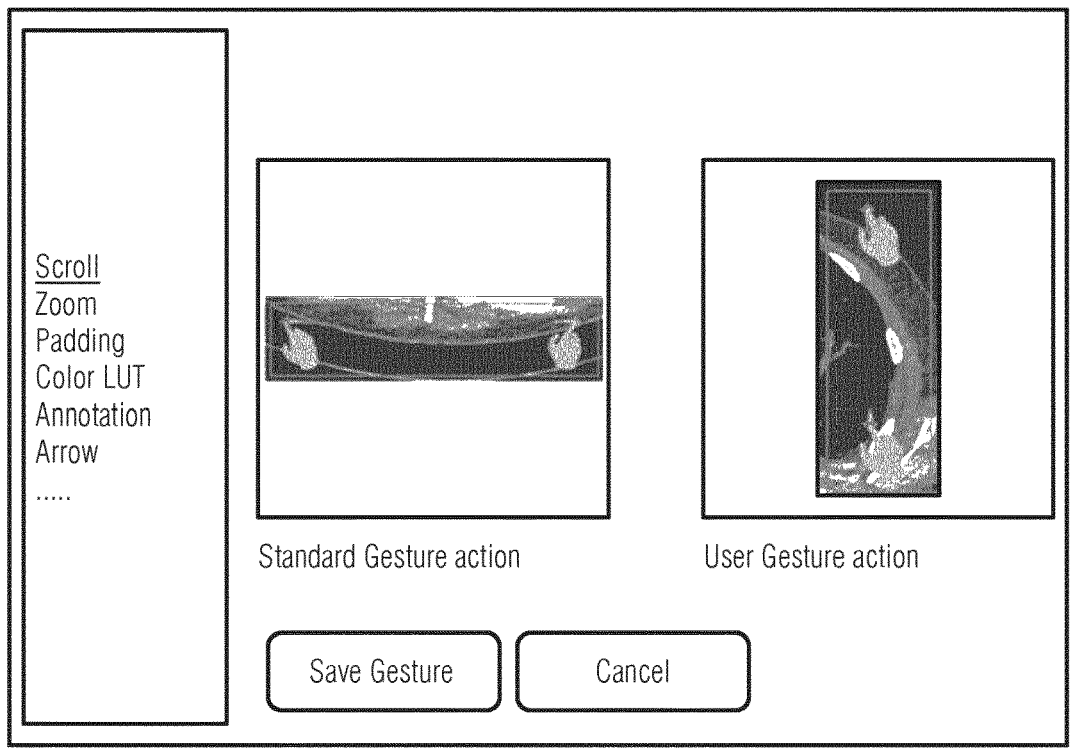

FIG. 5 shows an example window on the extended touch screen device 10 for DICOM image viewing gesture actions, like zooming, padding, color LUT, annotating, arrowing, etc. . . . . On the left hand side the standard gesture action is depicted and on the right hand side the user-configured gesture action is shown. The user is prompted with a button for saving his gesture choice or for cancelling the same. In the latter case, the standard gestures will be applied. Another example (not shown) relates to gestures for scrolling images. Usually, the standard gesture is a wiping movement in a horizontal direction over the screen from left to right. The user-configured gesture may be defined as a wiping gesture in a vertical direction, for example up to down or the other way from downwards down to upwards. Alternatively, it may be convenient to apply a wiping gesture in the other horizontal direction, namely form right to left, especially, if other buttons are to be activated immediately after the wiping gesture, which are positioned on the left hand side of the screen.

The invention claimed is:

1. A method for controlling a cloud-based image processing application, the method comprising:
   causing a touch screen device to display a user input configuration interface the user input configuration interface including a candidate user-specific gesture, a first standard gesture and a selectable interface element;
   generating a user input configuration based on information received via the user input configuration interface, the user input configuration including a mapping between a set of user-specific gestures and a set of standard gestures, and the set of standard gestures including the first standard gesture;
   registering the user input configuration for processing medical image data;
   receiving the medical image data and a user-specific gesture signal on the touch screen device;
   segregating PHI-data and non-confidential data among the medical image data;
   encrypting the PHI-data to obtain encrypted PHI-data decryptable at a cloud server;
   sending a data package to the cloud server, the data package including the encrypted PHI-data and the non-confidential data;
   receiving the user-specific gesture signal from the touch screen device;
   mapping the user-specific gesture signal to a corresponding standard gesture among the set of standard gestures based on the user input configuration;
   generating a control instruction based on the corresponding standard gesture; and
   processing the medical image data using the cloud-based image processing application at the cloud server according to the user-specific gesture signal based on the control instruction.

2. The method of claim 1, further comprising: receiving processed image data from the cloud server; and displaying the processed image data.

3. The method of claim 2, wherein the receiving the medical image data receives the medical image data from a storage.

4. The method of claim 2, wherein
   the method further comprises receiving the set of user-specific gestures
   corresponding to specific standard gestures among the set of standard gestures; and wherein
   the user-specific gesture signal corresponds to a user-specific gesture among the set of user-specific gestures for control of the cloud-based image processing application.

5. The method of claim 2, further comprising:
   transferring the user input configuration to the cloud server.

6. The method of claim 2, further comprising:
   transferring the user-specific gesture signal to the cloud server for processing the medical image data.

7. The method of claim 2, wherein the user-specific gesture signal causes the cloud-based image processing application to process the medical image data by:
   windowing, scrolling, sharing, zooming, inverting, coloring, selecting, padding or annotating, and wherein the user-specific gesture signal causes the selecting by tapping to select or dragging to select.

8. The method of claim 2, further comprising:
   updating the user input configuration by replacing an existing user-specific gesture among the set of user-specific gestures to obtain an updated input configuration; and
   storing the updated input configuration at the cloud server.

9. The method of claim 2, wherein the cloud server is part of a gesture support system including a plurality of distributed computer registerable entities; and the method further comprises notifying at least some of the plurality of distributed computer registerable entities in response to the cloud server receiving new image related data.

10. The method of claim 1, wherein the receiving the medical image data receives the medical image data from a storage.

11. The method of claim 10, wherein the method further comprises receiving the set of user-specific gestures corresponding to specific standard gestures among the set of standard gestures; and wherein the user-specific gesture signal corresponds to a user-specific gesture among the set of user-specific gestures for control of the cloud-based image processing application.

12. The method of claim 10, further comprising: transferring the user input configuration to the cloud server.

13. The method of claim 10, further comprising: transferring the user-specific gesture signal to the cloud server for processing the medical image data.

14. The method of claim 10, wherein the user-specific gesture signal causes the cloud-based image processing application to process the medical image data by: windowing, scrolling, sharing, zooming, inverting, coloring, selecting, padding or annotating, and wherein the user-specific gesture signal causes the selecting by tapping to select or dragging to select.

15. The method of claim 10, further comprising: updating the user input configuration by replacing an existing user-specific gesture among the set of user-specific gestures to obtain an updated input configuration; and storing the updated input configuration at the cloud server.

16. The method of claim 10, wherein the cloud server is part of a gesture support system including a plurality of distributed computer registerable entities; and the method further comprises notifying at least some of the plurality of distributed computer registerable entities in response to the cloud server receiving new image related data.

17. The method of claim 1, wherein the method further comprises receiving the set of user-specific gestures corresponding to specific standard gestures among the set of standard gestures; and wherein the user-specific gesture signal corresponds to a user-specific gesture among the set of user-specific gestures for control of the cloud-based image processing application.

18. The method of claim 1, further comprising: transferring the user input configuration to the cloud server.

19. The method of claim 1, further comprising:
transferring the user-specific gesture signal to the cloud server for processing the medical image data.

20. The method of claim 1, wherein the user-specific gesture signal causes the cloud-based image processing application to process the medical image data by:
windowing, scrolling, sharing, zooming, inverting, coloring, selecting, padding or annotating, and wherein the user-specific gesture signal causes the selecting by tapping to select or dragging to select.

21. The method of claim 1, further comprising:
updating the user input configuration by replacing an existing user-specific gesture among the set of user-specific gestures to obtain an updated input configuration; and
storing the updated input configuration at the cloud server.

22. The method of claim 1, wherein
the cloud server is part of a gesture support system including a plurality of distributed computer registerable entities; and
the method further comprises notifying at least some of the plurality of distributed computer registerable entities in response to the cloud server receiving new image related data.

23. A gesture support system for controlling a cloud-based image processing application, the gesture support system comprising:
a touch screen device configured to,
display a user input configuration interface, the user input configuration interface including a candidate user-specific gesture, a first standard gesture and a selectable interface element,
generate a user input configuration based on information received via the user input configuration interface, the user input configuration including a mapping between a set of user-specific gestures and a set of standard gestures, and the set of standard gestures including the first standard gesture,
register the user input configuration for processing medical image data,
access or receive the medical image data stored in a first storage,
segregate PHI-data and non-confidential image data among the medical image data,
encrypt the PHI-data to obtain encrypted PHI-data, and
send a data package to a cloud server, the data package including the encrypted PHI-data and the non-confidential image data; and the cloud server configured to,
decrypt the data package using an uploader service of the cloud server,
receive a user-specific gesture signal from the touch screen device,
map the user-specific gesture signal to a corresponding standard gesture among the set of standard gestures based on the user input configuration,
generate a control instruction based on the corresponding standard gesture, and
process the medical image data using the cloud-based image processing application by applying the control instruction.

24. The gesture support system of claim 23, wherein the touch screen device is configured to display at least one of the medical image data or a user-specific gesture among the set of user-specific gestures.

25. The gesture support system of claim 23, wherein the touch screen device is configured to receive the set of user-specific gestures corresponding to specific standard gestures among the set of standard gestures.

26. The gesture support system of claim 23, further comprising at least one of:
a second storage configured to store at least one of a decrypted image data package, the user input configuration or metadata relating to image processing;
a database;
a service bus; or
an authorization server configured to verify authorization of entities.

27. A gesture support system for controlling a cloud-based image processing application, the gesture support system comprising: a touch screen device configured to,
display a user input configuration interface the user input configuration interface including a candidate user-specific gesture, a first standard gesture and a selectable interface element,
generate a user input configuration based on information received via the user input configuration interface, the user input configuration including a mapping between a set of user-specific gestures and a set of standard gestures, and the set of standard gestures including the first standard gesture,
register the user input configuration for processing medical image data
access or receive the medical image data stored in a first storage,
segregate PHI-data and non-confidential image data among the medical image data,
encrypt the PHI-data to obtain encrypted PHI-data, and
send a data package including the encrypted PHI-data and the non-confidential image data to a cloud server; and the cloud server configured to,
decrypt the data package,
receive a user-specific gesture signal from the touch screen device,
map the user-specific gesture signal to a corresponding standard gesture among the set of standard gestures based on the user input configuration,
generate a control instruction based on the corresponding standard gesture, and
process the medical image data using the cloud-based image processing application by applying the control instruction.

28. The gesture support system of claim 27, wherein the touch screen device is configured to display at least one of the medical image data or a user-specific gesture among the set of user-specific gestures.

29. The gesture support system of claim 27, wherein the touch screen device is configured to receive the set of user-specific gestures corresponding to specific standard gestures among the set of standard gestures.

30. The gesture support system of claim 27, further comprising at least one of:
- a second storage configured to store at least one of a decrypted image data package, and the user input configuration or metadata relating to image processing;
- a database;
- a service bus; or
- an authorization server configured to verify authorization of entities.

* * * * *